United States Patent [19]

Gabriele et al.

[11] 4,030,719
[45] June 21, 1977

[54] CHILD IMMOBILIZING DEVICE FOR X-RAYS

[75] Inventors: William Joseph Gabriele; Joseph Michael Gabriele, both of Fenton, Mich.

[73] Assignee: Contour Fabricators, Inc., Fenton, Mich.

[22] Filed: Aug. 30, 1976

[21] Appl. No.: 718,943

[52] U.S. Cl. .............................................. 269/328
[51] Int. Cl.² ......................................... A61F 5/37
[58] Field of Search .......... 269/328, 322; 128/134, 128/133, 165

[56] References Cited

UNITED STATES PATENTS

| | | | |
|---|---|---|---|
| 2,751,268 | 6/1956 | Creelman | 269/328 |
| 3,358,141 | 12/1967 | Hoffmann et al. | 269/328 |
| 3,933,154 | 1/1976 | Cabansag | 269/328 |

*Primary Examiner*—James L. Jones, Jr.
*Assistant Examiner*—Robert C. Watson
*Attorney, Agent, or Firm*—Harness, Dickey & Pierce

[57] ABSTRACT

This disclosure relates to a device for immobilizing infants and young children during radiographic examination. The device consists of a cellular foam insert contoured with a cavity to partially envelop and restrain the child, restraining straps made from a foam and fabric combination, and a plastic base designed to support the foam insert and provide a fastening point for the restraining straps. All of the materials used in the device are radiolucent, thus showing no trace of shadows or foreign artifacts on radiographic film.

11 Claims, 2 Drawing Figures

CHILD IMMOBILIZING DEVICE FOR X-RAYS

BACKGROUND OF THE INVENTION

1. Field of the Invention

The present invention primarily to immobilizing devices for radiographic examination, and more particularly to immobilizing devices for infants and young children.

2. Description of the Prior Art

The state of the art is indicated by the following cited references: U.S. Pat. No. 749,457 — Gaiter, U.S. Pat. No. 2,700,381 — Powell, U.S. Pat. No. 2,751,268 — Creelman, U.S. Pat. No. 3,034,502 — Lund, U.S. Pat. No. 3,306,287 — Arp, U.S. Pat. No. 3,358,141 — Hoffman et al, U.S. Pat. No. 3,526,222 — Dreibelbis, U.S. Pat. No. 3,606,885 — Lund, U.S. Pat. No. 3,650,523 — Darby, Jr., U.S. Pat. No. 3,729,752 — Huggins, U.S. Pat. No. 3,861,666 — Nishiyama. Generally, immobilizing devices for use in radiographic examination have consisted of a wood or metal frame to which the patient was secured by means of restraining straps made of leather or the like. Not only have such devices been found to be clumsy in use, but also hae been found to shock and intimidate infants and young children, who usually begin to scream and cry when set on such a cold surface or secured in such a terrifying contraption. Some attempts have been made at designing immobilizing devices specifically for children, but these have not been accepted to any great extent by hospitals or X-ray laboratories. In fact, most such institutions use technicians with lead uniforms to manually hold the infant or young child during the examination. Not only must such technicians be paid at a competitive hourly rate, but also are present in the room while the X-rays are taken, and thus are susceptible to large quantities of harmful radiation.

In a addition to being clumsy, most prior art devices show up on radiographic film as shadows or foreign artifacts since they are not completely radiolucent. The presence of such shadows on X-rays may tend to distort or block out the desired images and thus impede effective diagnosis by a radiologist. As an alternative, many hospitals or X-ray laboratories currently use tape or the like to secure the patient, in place of using techincians to manually hold the patient. This alternative is very unsatisfactory.

It is a principal object of the present invention, therefore, to provide an improved immobility device for use in radiographic examination.

It is a further object of the present invention to provide an immobility device specifically for infants and young children.

It is another object of the present invention to provide an immobilizing device which is completely radiolucent.

Other objects, features and advantages of the present invention will become apparent from the subsequent description and the appended claims taken in conjunction with the accompanying drawings.

SUMMARY OF THE INVENTION

In accordance with the present invention, a child holder device for immobilizing infants and young children during radiographic examination is provided which is specially adapted to be easy to handle and to be completely radiolucent. The device consists of a cellular foam insert contoured with a cavity to partially envelop and restrain the child. Restraining straps made from a foam and fabric combination are fastened to a plastic base designed to support the foam insert.

BRIEF DESCRIPTION OF THE DRAWINGS

The foregoing objects and others apparent and in part pointed out more fully hereinafter in conjunction with the description of the preferred embodiment of the present invention illustrated in the accompanying drawings and in which.

DESCRIPTION OF THE PREFERRED EMBODIMENT

Figure 1:
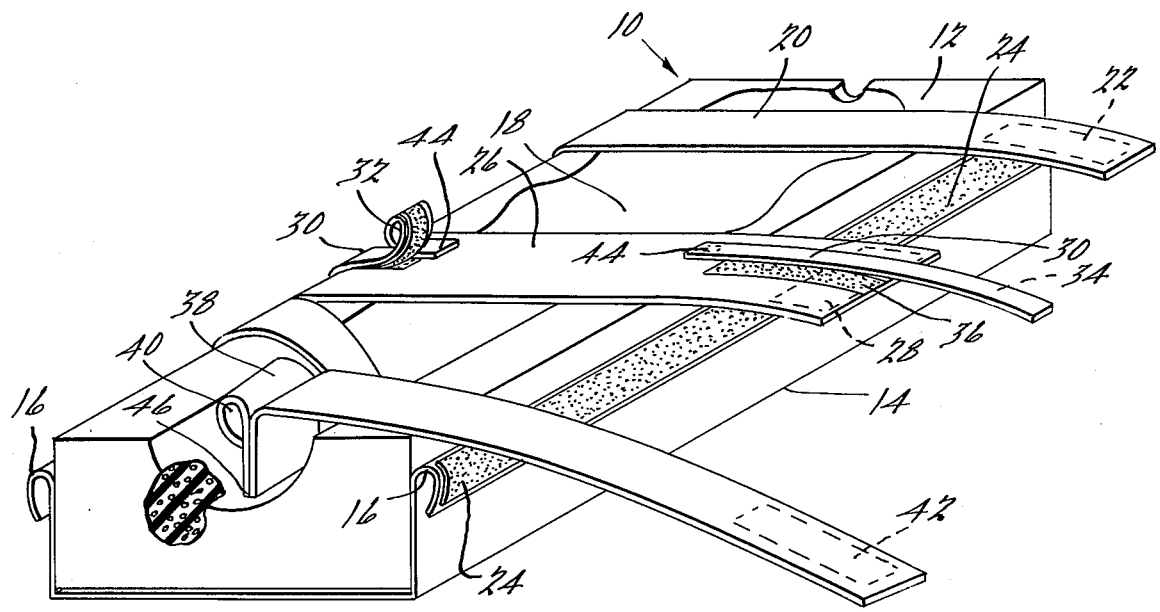
FIG. 1 is a perspective view of a preferred embodiment of the present invention, showing the restraining straps partially extended.
Figure 2:
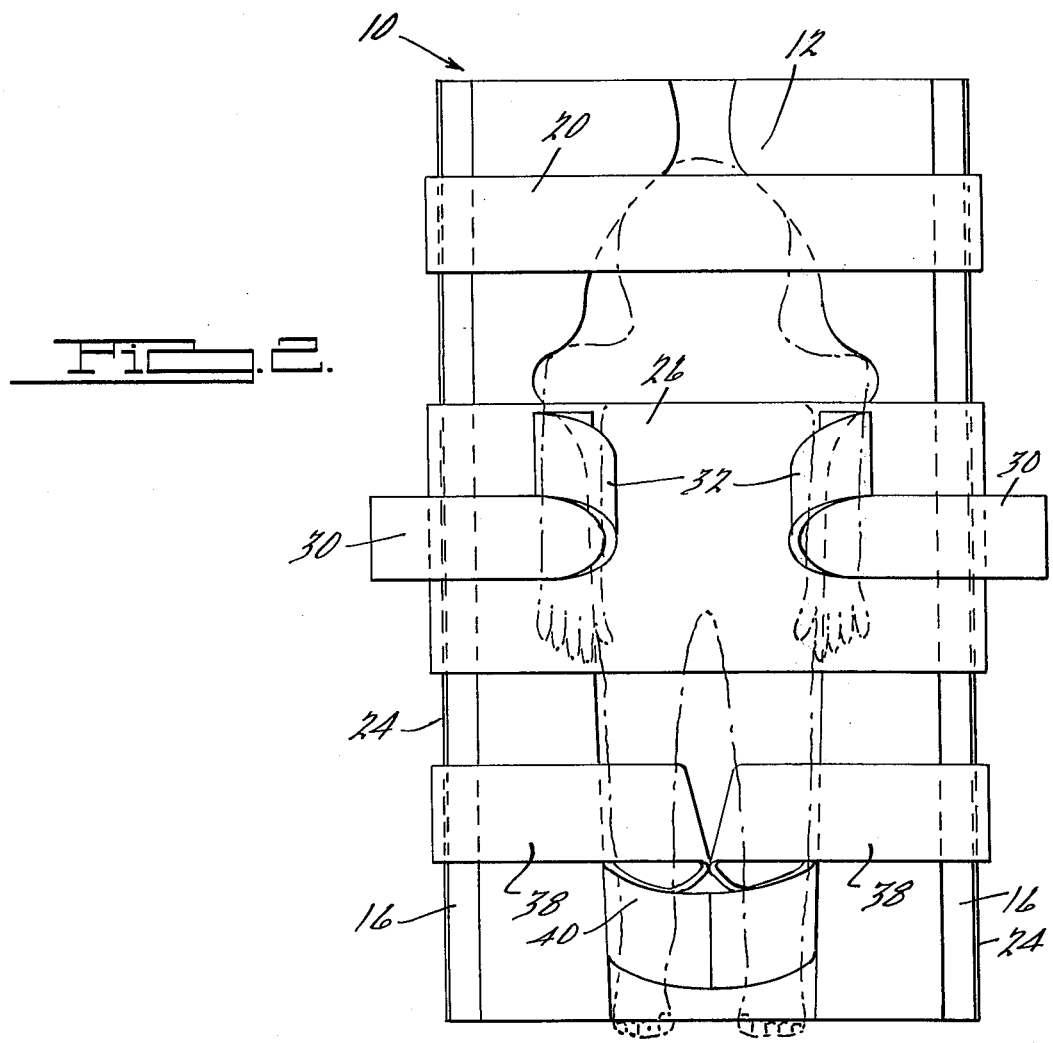
FIG. 2 is a top plan view of the present invention in use of immobilize a young child.

Referring now to the drawings, wherein the showings are for the purpose of illustrating a preferred embodiment of the invention only and are not for the purpose of limiting the invention, FIG. 1 shows a child holder device 10 wherein the cellular foam insert 12 is dimensioned in its width so as to be in an interference fit with the sides of plastic base 14 to keep said cellular foam insert 12 from sliding out of said plastic base 14. The plastic base 14 is comprised of a horizontal portion and two substantially vertical, longitudinal walls connected to said horizontal portion. The sides of the plastic base 14 are bent over at point 16 in an effort to eliminate any possibility of injury to a problem patient.

In the preferred embodiment shown in FIG. 1, a hook and loop type fastening system is used throughout the device. "Velcro" is an example of such a fastening system. Although other fastening systems may be used such as snap type fasteners or reusable pressure sensitive adhesives, few of these alternatives present all the advantages of the hook and loop system. Hook"Hook portions of the system are found at points 22, 28, 34 and 42, while "loop" portions of the system are found at points 24 and 36. The left half of the device is symmetrical to the right half of the device and contains similar portions.

When an infant or young child is placed in the device, they are positioned such that their head lies within the upper contoured portion of cavity 18. The shape and depth of the cavity 18 correspond roughly to the shape of the patient with the widest section being at the shoulders, and the depth being such that the patient is partially enveloped and restrained. Head restraining strap 20 is then positioned over the forehead of the patient and the "hook" strip 22 on the bottom side of strap 20 is secured to the "loop" strip 24, which runs the entire length of the device along the bent over lip of the plastic base 14. Chest restraining strap 26 is then positioned over the torso of the patient and the "hook" strip 28 on the bottom side of strap 26 is secured to the "loop" strip 24. The arms of the patient are then positioned on top of arm restraining straps 30, which straps are then looped around the arms of the patient as shown at loop 32. The "hook" strip 34 on the bottom side of arm strap 30 is then secured to "loop" strip 36. The legs of the patient are then positioned below and on either side of leg restraining straps 38, which straps are then looped around the legs of the patient as shown at loop 40. The "hook" 42 on the bottom side of leg strap 38 is then secured to "loop" strip 24.

Head restraining strap 20 and chest restraining strap 26 are completely removable from the device. Arm restraining straps 30 are permanently attached to chest restraining strap 26 at points 44. Leg restraining staps 38 are permanently attached to one another below slot 46 in cellular foam insert 12. The leg restraining staps 38 are fed through slot 46 and attached to plastic base 14 by a hook and loop fastening system or the like.

It should be noted that due to the loops at points 32 and 40 through which the arms and legs pass respectively, any effort on the part of the patient to remove his arm or leg from the loop, or any effort to move his arm or leg away from the device will increase the holding force exerted by the strap. This of course greatly increases the immobilizing capacity of the device, and thus makes it even more attractive to potential users.

The plastic base 14 may be formed of any suitable plastic. Acrylic sheet stock, commonly known as plexiglas, has been found to present a good number of advantages including easy formability and attractive appearance.

The cellular foam insert 12 may be formed of any suitable foam elastomer. Polyurethane foam has been found to present several advantages. It is lightweight and soft textured, and also possesses innate thermal characteristics in that it absorbs, retains and emits body, room and incubator temperatures. The texture and temperature of the polyurethane insert make it "womb-like" in nature, creating a sense of security and warmth, thus resulting in partial pacification of the infant or young child. The polyurethane foam used should have high tear resistance and tensile strength, be flame resistant and not plasticize. In general, most polyurethane foams of this particular type offer high resilience and good fatigue resistance, and can be easily cleaned or sterilized by washing, boiling, or autoclaving. A plastic liner may also be used over the insert to guard against urine being absorbed into the foam, although such polyurethane foam is generally sanitary and non-nutrient for bacteria.

The restraining straps may be formed of any strong, durable material, but a combination of nylon taffeta coated with a thin layer of polyurethane foam has proven to be very acceptable. The straps are formed by sewing pieces of the nylon-foam combination together in such a way as to produce straps with only foam on the outside surfaces. The straps are located so as not to interfere with the radiographic examination.

The use of the materials herein recommended has been shown to produce a child holder device which is completely radiolucent in the normal energy range of X-ray radiation, that is, between 50 to 250 keV. No trace of shadows or foregin artifacts has been shown at any angle of use. The device has been shown to be especially effective and useful in the following radiographic, pediatric examinations: 1) skull series AP's and laterals, 2) flat, upright and lateral abdomen and chest, 3) all cross-table work, 4) all extremities, 5) "frog-leg" hip, and 6) when used as an immobilizer for IVP's and circumcisions.

While it will be apparent that the preferred embodiment of the invention disclosed is well calculated to fulfill the objects above stated, it will be appreciated that the invention is susceptible to modificaton, variation and change without departing from the proper scope or fair meaning of the subjoined claims.

We claim:

1. An immobilizing device for use in medical procedures which comprises:

a cellular foam insert contoured with a cavity adapted to partially envelop and restrain a patient;

a plurality of restraining strap means to provide an immobilizing force on the patient;

a rigid base designed to support said cellular foam insert wherein said rigid base is comprised of a horizontal portion and two substantially vertical, longitudinal walls connected to said horizontal portion; and a fastening means used to secure said plurality of restraining straps to said rigid base.

2. The immobilizing device of claim 1 wherein said cellular foam insert is made of polyurethane foam.

3. The immobilizing device of claim 1 wherein said plurality of restraining straps comprises a head restraining strap, a chest restraining strap to which are fastened two arm restraining straps, and two leg restraining straps.

4. The immobilizing device of claim 1 wherein said plurality of restraining straps are made of a foam and fabric combination.

5. The immobilizing device of claim 1 wherein said plurality of restraining straps are made of nylon taffeta coated with a thin layer of polyurethane foam.

6. The immobilizing device of claim 1 wherein said plurality of restraining strap means are looped around the patient's arms and legs to provide an immobilizing force which increases if the patient exerts any effort to remove his arms or legs.

7. The immobilizing device of claim 1 wherein said rigid base is made of plastic.

8. The immobilizing device of claim 1 wherein said rigid base is made of acrylic plastic.

9. The immobilizing device of claim 1 wherein said fastening means is a hook and loop type fastening system.

10. The immobilizing device of claim 1 wherein all the materials used to construct the device are radiolucent.

11. A child immobilizing device for use in medical procedures which comprises:

a radiolucent polyurethane foam insert contoured in shape and depth to correspond roughly to the shape of the patient with the widest section being opposite the patient's shoulders, and the depth being such that the patient is partially enveloped and restrained;

a plurality of radiolucent restraining straps made of nylon taffeta coated with a thin layer of polyurethane foam, said plurality of restraining straps comprising a head restraining strap, a chest restraining strap to which are fastened two arm restraining straps, and two leg restraining straps, said arm and leg restraining straps being looped around the patient's arms and legs respectively, to provide an immobilizing force which increases if the patient exerts any effort to remove his arms or legs;

a radiolucent rigid vase made of acrylic plastic designed to support said polyurethane foam insert wherein said rigid base is comprised of a horizontal portion and two substantially vertical, longitudinal walls connected to said horizontal portion, said vertical side walls being bent 180° to form a curved upper edge; and a radiolucent hook and loop type fastening system used to secure said plurality of restraining straps to said rigid base wherein hook portions are found on the underside of the head, chest, arm and leg restraining straps, and mating loop portions are found on the chest restraining strap and along the bent over vertical side edges of said rigid base.

* * * * *

UNITED STATES PATENT AND TRADEMARK OFFICE
CERTIFICATE OF CORRECTION

PATENT NO. : 4,030,719
DATED : June 21, 1977
INVENTOR(S) : William Joseph and Joseph Michael Gabriele It is certified that error appears in the above-identified patent and that said Letters Patent are hereby corrected as shown below:

```
Column 1, line 24, the word "hae" should read as -- have --;
Column 1, line 33, insert after "during the" the word
    -- x-ray --;
Column 1, line 38, the phrase "In a addition" should read
    as -- In addition --;
Column 1, line 49, the word "immobility" should read as
    -- immobilizing --;
Column 1, line 52, the word "immobility" should read as
    -- immobilizing --;
Column 1, line 52, after the word "device" insert the
    word -- designed --;
Column 2, line 6, after the word "others" insert the
    following -- will in part be --;
Column 2, line 15, the word "of" should read as -- to --;
Column 2, line 39, the words "Hook"Hook" should read as
    -- "Hook" --;
Column 2, line 67, insert the word "strip" after the
    word -- "hook" --;
Column 3, line 6, the word "staps" should read as -- straps --
Column 4, line 55, the word "vase" should read as -- base --.
```

Signed and Sealed this

Fourth Day of October 1977

[SEAL]

Attest:

RUTH C. MASON
*Attesting Officer*

LUTRELLE F. PARKER
*Acting Commissioner of Patents and Trademarks*